(12) United States Patent
Tamblyn et al.

(10) Patent No.: US 8,010,379 B2
(45) Date of Patent: Aug. 30, 2011

(54) PATIENT CARE MANAGEMENT SYSTEMS AND METHODS

(75) Inventors: Robyn Tamblyn, Montreal (CA); Allen Huang, Montreal (CA); Jimmy Fragos, Laval (CA); Mélodie Faucher, Montreal (CA); Nadyne Girard, St. Bruno (CA)

(73) Assignee: McGill University, Montreal, QC (CA)

( * ) Notice: Subject to any disclaimer, the term of this patent is extended or adjusted under 35 U.S.C. 154(b) by 1396 days.

(21) Appl. No.: 10/974,480

(22) Filed: Oct. 27, 2004

(65) Prior Publication Data

US 2005/0144038 A1  Jun. 30, 2005

Related U.S. Application Data

(60) Provisional application No. 60/515,706, filed on Oct. 31, 2003.

(30) Foreign Application Priority Data

Oct. 31, 2003  (CA) .................................... 2447864

(51) Int. Cl.
  *G06Q 10/00* (2006.01)
  *G06Q 50/00* (2006.01)
(52) U.S. Cl. ......................................................... 705/2
(58) Field of Classification Search .................. 705/2, 3, 705/4, 236
  See application file for complete search history.

(56) References Cited

U.S. PATENT DOCUMENTS

| | | | | |
|---|---|---|---|---|
| 5,737,539 | A | * | 4/1998 | Edelson et al. .................... 705/3 |
| 6,004,020 | A | * | 12/1999 | Bartur ............................ 700/236 |
| 6,208,973 | B1 | * | 3/2001 | Boyer et al. ....................... 705/2 |
| 6,578,003 | B1 | | 6/2003 | Camarda et al. |
| 7,072,840 | B1 | | 7/2006 | Mayaud |
| 2005/0144039 | A1 | | 6/2005 | Tamblyn |

OTHER PUBLICATIONS

Wilchesky, et al., "Validation of Diagnostic Codes Within Medical Services Claims", McGill University, Faculty of Medicine, pp. 1-33, Feb. 2004.
Tamblyn, et al., "Physician and Practice Characteristics Associated with the Early Utilization of New Prescription Drugs", Medical Care, vol. 41, No. 8, pp. 895-908 (2003).
Tamblyn, et al., "Association Between Licensure Examination Scores and Practice in Primary Care", American Medical Association, (reprinted) JAMA, vol. 288, No. 23, pp. 3019-3026 (Dec. 18, 2002).

(Continued)

*Primary Examiner* — Gerald J. O'Connor
*Assistant Examiner* — John Pauls
(74) *Attorney, Agent, or Firm* — Benoît & Côté

(57) ABSTRACT

A patient care management system for assisting a physician in monitoring drug use by a patient. The system receives drug dispensation data for a drug, on the basis of which the system determines drug supply availability data. The drug supply availability data is indicative of periods of time during which the drug was available in non-duplicate supply, or in oversupply, or in insufficient supply. The periods of time are displayed with respect to a common time base. Each degree of supply availability is visually displayed via a graphical user interface using, e.g., a color coded scheme, so as to be distinguishable by a user. This allows a physician to rapidly assess over-consumption or compliance problems. Plural drugs may be monitored on a single display screen. The system may also be adapted to allow an prescribing physician to assess refill compliance, hospitalization periods and prescription drug costs.

43 Claims, 6 Drawing Sheets

OTHER PUBLICATIONS

Tamblyn, et al., "Adverse Events Associated With Prescription Drug Cost-Sharing Among Poor and Elderly Persons", American Medical Association, (reprinted) JAMA, vol. 285, No. 4, pp. 421-429 (Jan. 24/31, 2001).

Tamblyn, et al., "Using Medical Services Claims to Assess Injuries in the Elderly: Sensitivity of Diagnostic and Procedure Codes for Injury Ascertainment", Journal of Clinical Epidemiology 53, pp. 183-194 (2000).

Tamblyn, et al., "Association Between Licensing Examination Scores and Resource Use and Quality of Care in Primary Care Practice", JAMA, vol. 280, No. 11, pp. 989-996 (Sep. 16, 1998).

Tamblyn, et al., "The Use of Prescription Claims Database in Pharmacoepidemiological Research: The Accuracy and Comprehensiveness of the Prescription Claims Database in Quebec", Pergamon, J. Clin Epidemiol, vol. 48, No. 8, pp. 999-10009 (1995).

* cited by examiner

PATIENT CARE MANAGEMENT SYSTEMS AND METHODS

CROSS-REFERENCES TO RELATED APPLICATION

The present application claims the benefit under 35 U.S.C. 119(e) of U.S. Provisional Patent Application Ser. No. 60/515,706, filed Oct. 31, 2003, hereby incorporated by reference herein.

FIELD OF THE INVENTION

The present invention relates generally to the field of patient care management and, more particularly, to systems and methods for assisting physicians in their treatment of patients.

BACKGROUND OF THE INVENTION

In modern-day society, individuals have the freedom to choose the physician by whom they wish to be treated for a given medical condition. Since an individual may require the attention of more than one specialized medical professional, it may thus happen that the patient is seen by two or more physicians for the same or different medical conditions. Each physician may prescribe one or more drugs, with goals as diverse as treating a condition, mitigating a symptom, relieving pain, etc. If a patient is prescribed multiple drugs, there is a risk that some of the drugs may adversely interact with one another. Such drugs are said to be contraindicated. Moreover, if the patient is being seen for multiple medical conditions, then the drug prescribed for one condition may cause an adverse side effect due to another condition with which the patient is afflicted.

Of course, a physician will usually try to take the risk of side effects into consideration when prescribing a drug. Still, there is a possibility for human error when performing a contraindications verification, for example. A compounding factor is the sheer amount of medical knowledge that a physician has to think about when delivering medical care. Moreover, physicians will generally be unaware of what drugs the patient may have been prescribed by other physicians or for what other ailment the patient may have sought treatment from another physician. Asking the patient for this information may be considered as one solution but can lead to incomplete or incorrect information which may lead to the issuance of an inappropriate prescription. Clearly, therefore, the risk of an adverse medication side effect is greatly increased when a patient is seen by multiple physicians and is prescribed multiple drugs, a scenario not at all uncommon. It would thus be desirable to manage information regarding prescribed drugs in order to assist a physician in treating a patient and improve appropriate prescribing.

Furthermore, a physician's ability to gauge the effectiveness of a drug is often conditional upon the patient's regular intake of a prescribed dosage, followed by a check-up. If the patient has neglected to refill a prescription in the meantime, or has been using more than the originally prescribed dosage of the drug by obtaining a supplemental prescription from another physician/pharmacy, this may skew the physician's assessment of the effectiveness of a drug, leading to, potentially, an erroneous diagnosis and the issuance of further prescriptions that may not be appropriate for the situation at hand. It would thus be desirable to provide a way to monitor prescription drug use in order to assist physicians to more accurately assess the effectiveness of therapy and to avoid unintentional over-prescribing.

SUMMARY OF THE INVENTION

The present invention seeks to provide integrated and informative drug and clinical data to enable physicians to provide appropriate prescribing for their patients.

According to a first broad aspect, the present invention seeks to provide a patient care management system. The system comprises an input adapted to receive drug dispensation data for at least one drug, a control entity adapted to determine drug supply availability data for the at least one drug on the basis of the drug dispensation data and an output adapted to release the drug supply availability data for the at least one drug.

According to a second broad aspect, the present invention seeks to provide a patient care management system. The system comprises an input adapted to receive data regarding a plurality of drugs dispensed or prescribed to the patient. The system also comprises a control entity adapted to determine groups of pharmacologically equivalent drugs from the plurality of drugs dispensed or prescribed to the patient and to combinedly process the data regarding the drugs in each group of pharmacologically equivalent drugs.

The system further comprises an output adapted to release the combinedly processed data.

According to a third broad aspect, the present invention seeks to provide a patient care management system. The system comprises an input for receiving data regarding a plurality of drugs dispensed to the patient, a control entity adapted to perform a drug-drug contraindications verification of the drugs dispensed to the patient and an output adapted to release data indicative of the drug-drug contraindications verification.

According to a fourth broad aspect, the present invention seeks to provide a patient care management system. The system comprises an input entity adapted to receive data regarding at least one insurance claim for medical services, a control entity adapted to determine from the data regarding the at least one insurance claim for medical services a feature of the medical services claimed in the at least one insurance claim and an output entity adapted to release data indicative of the feature of the medical services claimed in the at least one insurance claim.

According to a fifth broad aspect, the present invention seeks to provide a patient care management system. The system comprises a graphical user interface adapted to present to a user via a display data regarding at least one drug prescribed or dispensed to the patient. The system also comprises a control entity operative to receive a user selection of a particular one of the at least one drug prescribed or dispensed to the patient and access from a remote location new data regarding the particular drug. The graphical user interface is further adapted to present to the user via the display the new data regarding the particular drug.

According to sixth, seventh, eighth, ninth and tenth broad aspects, the present invention seeks to provide a computer-readable storage medium containing a program element for execution by a computing device to implement any of the above a patient care management systems described in accordance with the first, second, third, fourth and fifth broad aspects, respectively.

According to an eleventh broad aspect, the present invention seeks to provide a method of implementing a graphical user interface suitable for use in patient care management. The method comprises receiving data regarding a first period of time representative of a drug being available to a first degree of availability, receiving data regarding a first period of time representative of the drug being available to a second degree of availability different from the first degree of availability, displaying the first and second periods of time with respect to a common time base and providing a visual indication to allow a user to distinguish between the first and second periods of time.

According to a twelfth broad aspect, the present invention seeks to provide a method of implementing a graphical user interface suitable for use in patient care management. The method comprises receiving data regarding a first manner of dispensing a first one of at least one prescription drug over a first period of time, receiving data regarding a second manner of dispensing period of a second one of the at least one prescription drug over a second period of time, displaying the first and second periods of time with respect to a common time base and providing a visual indication to allow a user to distinguish between the first and second manners of dispensing.

According to a thirteenth broad aspect, the present invention seeks to provide a method of implementing a graphical user interface suitable for use in patient care management. The method comprises receiving data regarding at least one drug dispensed to the patient, receiving data regarding at least one drug prescribed but not dispensed to the patient and jointly displaying the data regarding the at least one drug dispensed to the patient and the data regarding the at least one drug prescribed but not dispensed to the patient.

According to a fourteenth broad aspect, the present invention seeks to provide a method of implementing a graphical user interface suitable for use in patient care management. The method comprises receiving data regarding a plurality of drugs dispensed to the patient, wherein the data regarding each particular drug includes an identity of a prescribing physician for the particular drug, receiving data regarding the identity of a prescribing physician and displaying data regarding the drugs dispensed to the patient by providing a visual indication that allows a user to distinguish between drugs for which the prescribing physician is the prescribing physician and drugs for which the prescribing physician is a physician other than the prescribing physician.

According to fifteenth, sixteenth, seventeenth and eighteenth broad aspects, the present invention seeks to provide a computer-readable storage medium containing a program element for execution by a computing device to implement any of the above methods described in accordance with the eleventh, twelfth, thirteenth and fourteenth fourth broad aspects, respectively.

These and other aspects and features of the present invention will now become apparent to those of ordinary skill in the art upon review of the following description of specific embodiments of the invention in conjunction with the accompanying drawings.

DETAILED DESCRIPTION OF THE EMBODIMENTS

Figure 1:
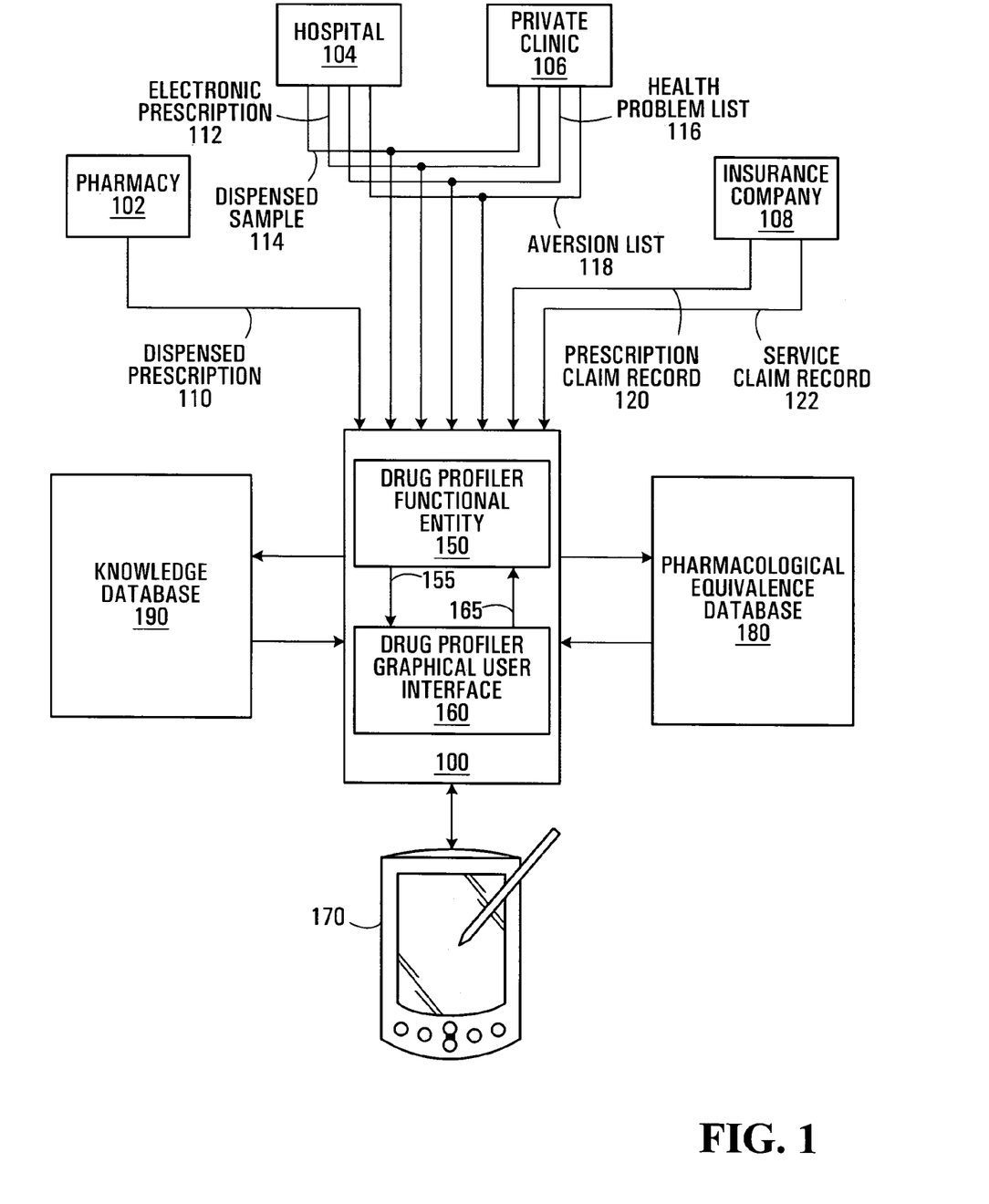
FIG. 1 shows a patient care management system in accordance with an embodiment of the present invention.

With reference to FIG. 1, there is shown a health care architecture including a patient care management system 100 that is connected to a plurality of information sources 102, 104, 106, 108. The patient care management system 100 may reside on a secure server that is managed by a government-accredited health care management company. The information sources 102, 104, 106, 108 may be broken down into three main types, namely remote clinical sources (e.g., a pharmacy 102), local clinical sources (such as a hospital 104 or a private clinic 106, etc.) and administrative sources (e.g., an insurance company 108). The information sources 102, 104, 106, 108 provide the patient care management system 100 with data of varying types and in varying formats. The manner in which the data is conveyed forms no part of the present invention and may include a dedicated link, a secure virtual private network (VPN), an encrypted internet session, a password-protected data exchange, etc.

In the case where the information source is a remote clinical source such as pharmacy 102, the data provided to the patient care management system 100 may take the form of dispensed prescription records 110, where each dispensed prescription record 110 identifies a patient, a drug dispensed to the patient, the date on which the drug was dispensed, a quantity dispensed, a duration of the prescription (e.g., by way of a number of allowed refills) and a dosage. In a variant, the drug and the dosage may be jointly represented by a drug identification number (DIN) or Digital Object Identification (DOI) number. Additional data such as the cost of the drug, the insured individual's contribution (cost share) and the identity of the prescribing physician may also be included.

In the case where the information source is a local clinical source such as hospital 104 or private clinic 106, the data provided to the patient care management system 100 may be in the form of electronic prescription records 112, where each electronic prescription record 112 identifies a patient, a prescribing physician, a drug prescribed to the patient, the date of the prescription, a quantity prescribed, a duration of the prescription and a dosage. In many cases, physicians dispense samples and thus the data provided to the patient care management system 100 may also be in the form of drug sample records 114 entered by the physician dispensing the sample. Each drug sample record 114 identifies a patient, the sample drug, the identity of the physician dispensing the sample, the date on which the sample was dispensed, the quantity dispensed, the duration of the sample and the dosage. An expected duration of the sample may also be output or it may readily be computed from the quantity dispensed and the dosage. Other data that may be supplied by a local clinical source include a health problem list indicative 116 of ailments with which the patient is afflicted as well as a list of drugs to which the patient is allergic or with respect to which the patient is intolerant, which can be referred to as an "aversion list" 118.

In the case where the information source is an administrative source such as an insurance company 108, the data provided to the patient care management system 100 may take the form of prescription claim records 120 similar to the dispensed prescription records 110 provided by a remote clinical source such as pharmacy 102. Accordingly, each prescription claim record 120 identifies a patient, a drug dispensed to the patient, the date on which the drug was dispensed, a quantity dispensed, a duration of the prescription (e.g., by way of a number of allowed refills), a dosage, the cost of the drug, the insured individual's contribution (cost share) and the identity of the prescribing physician. Each prescription claim record 120 also typically includes the location where the drug was dispensed, e.g., pharmacy identity, etc. In addition, an administrative information source may provide the patient care management system 100 with medical service claim records 122 that specify a type of medical service performed (e.g., medical or surgical procedure, etc.), as well as the date on which the service was performed and a location where the service was performed (e.g., ER, inpatient, outpatient). Since the administrative source maintains data regarding beneficiaries, the prescription claim records 120 and the medical service claim records 122 of medical services may be supplemented with additional data such as the age of the insured individual.

In an embodiment of the present invention, the patient care management system 100 implements a "drug profiler" that includes a drug profiler functional entity 150 and a drug profiler graphical user interface 160. The drug profiler functional entity 150 is responsible for processing data received from the various information sources 102, 104, 106, 108 and producing an output 155. The drug profiler graphical user interface 160 is responsible for presenting the output 155 received from the drug profiler functional entity 150 on a display 170. Non-limiting examples of a suitable display 170 include a PDA, tablet PC, laptop display, desktop display, touch screen, pen-based computer and so on. Also, the drug profiler graphical user interface 160 receives input from a user (typically, a prescribing physician) via a mouse, keyboard, electronic stylus, finger pressure on the display 170, etc., which is fed as an input 165 to the drug profiler functional entity 150. The drug profiler functional entity 150 re-processes the input 165, resulting in a new output 155 provided to the drug profiler graphical user interface 160, for presentation on the display 170.

In a first embodiment of the drug profiler, the data processed by the drug profiler functional entity 150 includes "drug dispensation data" regarding a particular drug that has been dispensed to a patient. The drug dispensation data is contained in the dispensed prescription records 110 received from a remote clinical source such as pharmacy 102. As previously described, each dispensed prescription record 110 identifies a patient, a drug dispensed to the patient, the date on which the drug was dispensed, a quantity dispensed, a duration of the prescription (e.g., by way of a number of allowed refills) and a dosage.

Figure 2A:
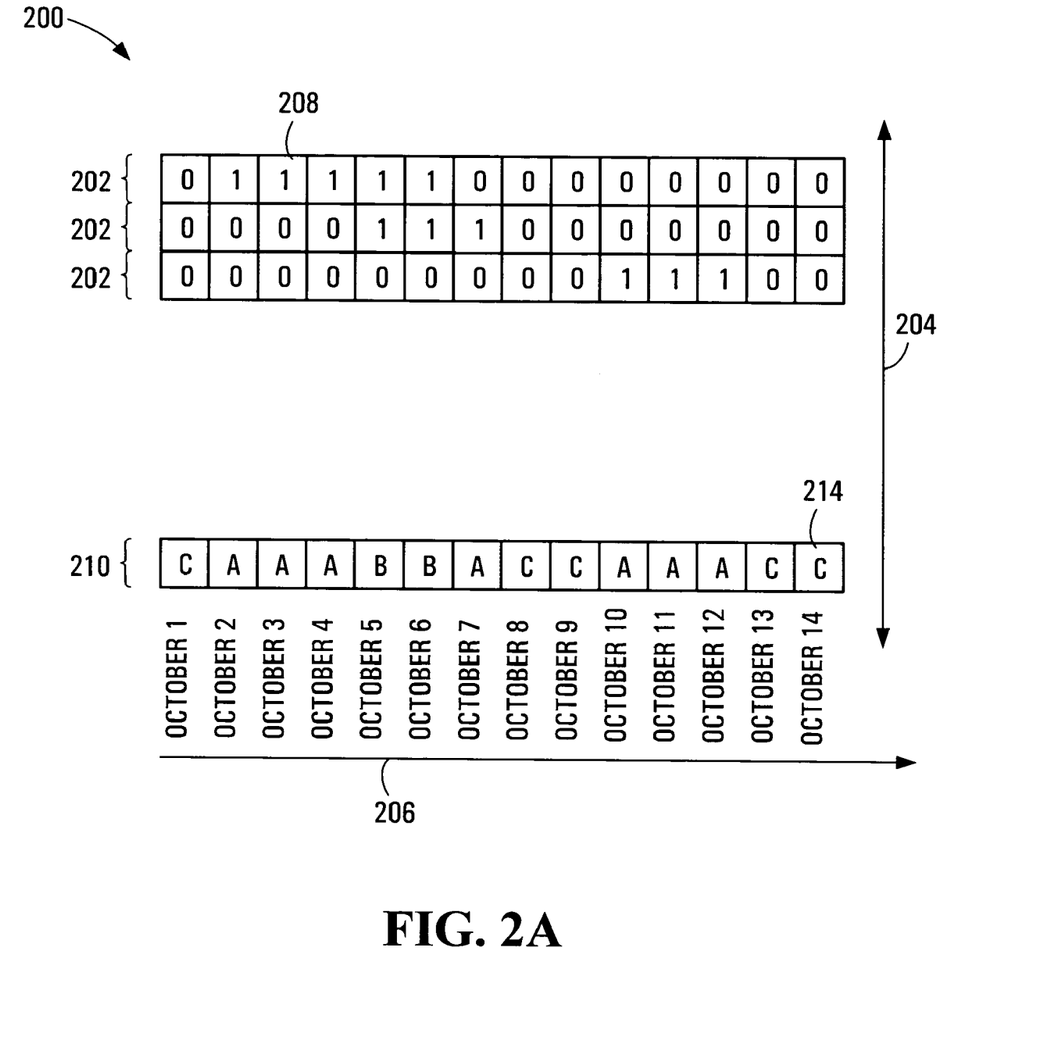
FIGS. 2A, 2B and 2C illustrate creation of a drug supply matrix, in accordance with embodiments of the present invention.

On the basis of the drug dispensation data, the drug profiler functional entity 150 computes "drug supply availability data" for each drug. With reference to FIG. 2A, the drug supply availability data is encoded in a drug supply matrix 200 which shows the calendar days in which the supply for the drug in question is expected to be available. The drug supply matrix 200 has an x-axis 206 and a y-axis 204. To create the drug supply matrix 200, all dispensed prescription records 110 pertaining to the drug in question are identified and grouped together as rows 202 of the drug supply matrix 200. For its part, the x-axis 206 represents calendar days (in thus case, October 1 though October 14). The drug supply matrix 200 thus has a matrix entry 208 for each calendar day and each row 202. Specifically, each matrix entry 208 corresponding to a given calendar day on the x-axis 206 and a given one of the rows 202 on the y-axis 204 contains an indication of supply availability. In one embodiment, this indication takes the form of a code, such as 1=supply available and 0=no supply available. The start date for supply availability along a given a row 202 is the date on which the drug was dispensed (obtained from the corresponding dispensed prescription record 110), while dosage and the quantity dispensed are used to compute an end date for supply availability along the row 202. In another embodiment, the end date may already be indicated in the corresponding dispensed prescription record.

When multiple rows 202 are present for the same drug, the drug profiler functional entity 150 consolidates the matrix entries 208 of the drug supply matrix 200 to create a "drug supply timeline" 210 which is another row along the x-axis 206 with entries 214 for each calendar day, each entry 214 being indicative of a day of non-duplicated supply, a day of oversupply or a day of insufficient supply of the drug. In a specific embodiment, the various degrees of supply availability are coded alphanumerically and are derived as follows. Entries 214 corresponding to days of non-duplicated supply, which is typically the most desirable case, contain a "A" if they correspond to calendar days for which exactly one matrix entry 208 contains a "1". When two or more matrix entries 208 for a given calendar day contain a "1", this is indicative of the drug being in oversupply on the given calendar day, resulting in a "B" being inserted in the corresponding entry 214 of the drug supply timeline 210. Finally, when none of the matrix entries 208 for a given calendar day contain a "1", this is indicative of the drug expected to be in insufficient supply on the given calendar day, resulting in a "C" being inserted in the corresponding entry 214 of the drug supply timeline 210.

The drug profiler graphical user interface 160 then supplies the data contained in the drug supply timeline 210 to the display 170, for presentation in a user-friendly manner. In a non-limiting example embodiment, the data contained in the drug supply timeline 210 may be represented by a bar graph that is color- and intensity-coded according to the value in each entry 214. Time periods corresponding to the various types of supply days, if more than one is applicable for the drug in question, are thus rendered visually distinguishable. This may prove useful in helping the user to identify a consumption problem (e.g., overuse) or to identify a potential problem with patient compliance.

Figure 3:
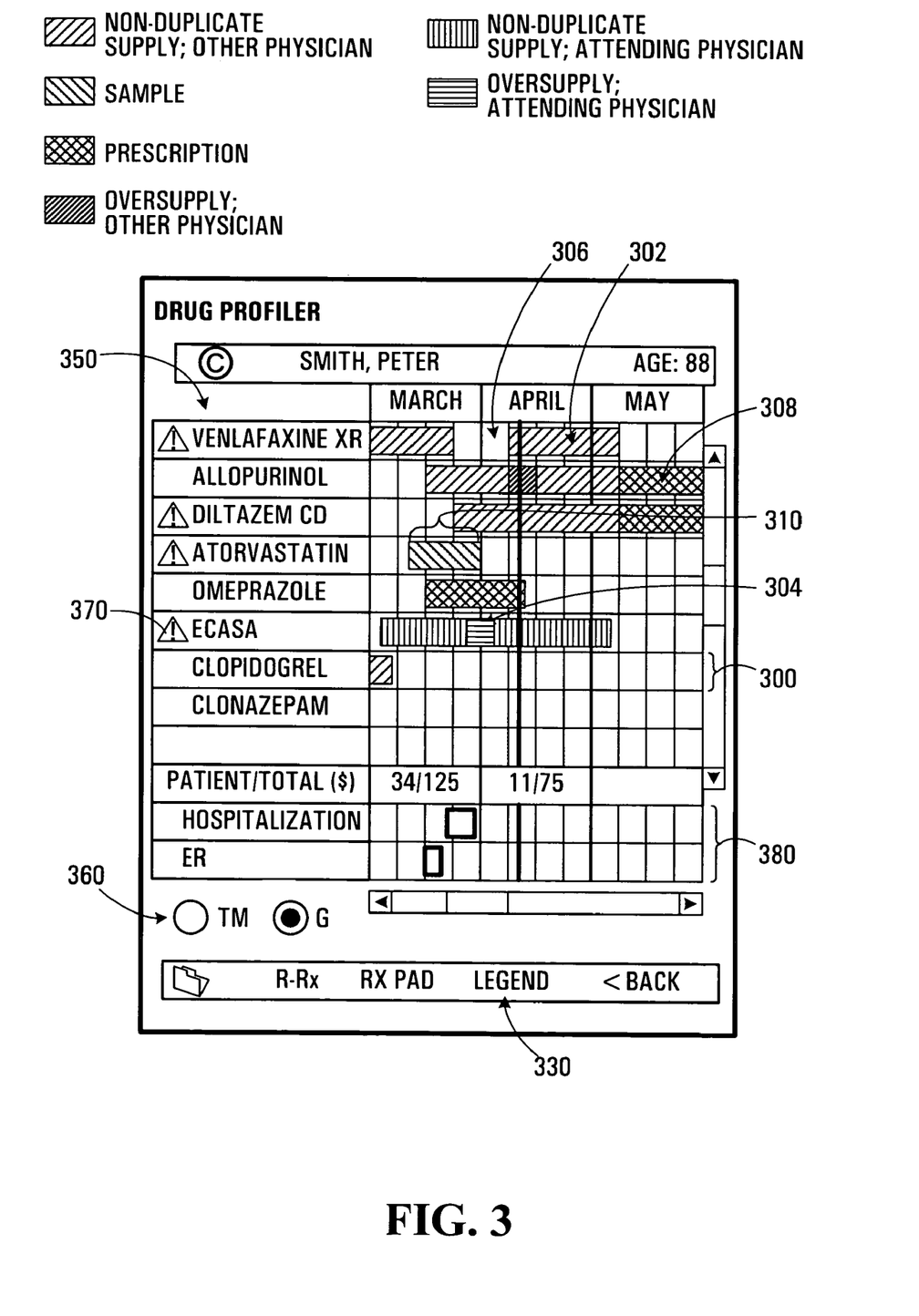
FIG. 3 shows an example screen shot presented via a display to a user of the patient care management system.

For example, with reference to FIG. 3, which shows a screen shot of the drug profiler display, days of non-duplicated supply (represented by entries 214 containing "A" in the drug supply timeline 210) may be indicated by a continuous portion 302 of a bar 300 that is given a particular color (or shade of grey, for monochromatic displays). Days of oversupply (represented by entries 214 containing "B" in the drug supply timeline 210) may be indicated by a continuous portion 304 of the bar 300 in a darker shade of the same color, allowing a user to assess if there is over-use of the drug. In an alternative that may be more effective with viewers of monochromatic displays, days of oversupply may be indicated by a temporary change in height of the portion 304 of the bar 300, while retaining the same shade and color. Finally, days of insufficient supply (represented by entries 214 containing "C" in the drug supply timeline 210) may be shown as a continuous portion 306 of the bar 300 that is given a completely different background color, lending the appearance of a "gap", and allowing a user to assess whether there may potential problems in patient compliance.

Of course, the use of the bar 300 is not to be interpreted as a limiting feature of the drug profiler graphical user interface 160, but merely illustrative of a suitable graphical technique that permits different degrees of supply availability to be visually distinguishable. Those skilled in the art will find it a matter of routine to experiment with different graphical representations until a particular such representation is found to be suitable for a particular application.

Other features of the displayed data may be controlled through interaction of the user with the drug profiler graphical user interface 160. The bar 300 or, generally, the visual representation of the drug supply timeline, may span a selectable time window, such as 1, 3, 6, 9 or 12 months, for example. By changing the time window (e.g., clicking an icon on the screen or touching a portion of the screen), the drug profiler graphical user interface 160 will cause a corresponding change (e.g., compression or expansion) in the bar 300 shown on the display 170.

Also, a legend to help distinguish the various shades and colors is accessible upon the user selecting a legend icon 330 from a menu or touching a portion of the screen. In an embodiment, the drug profiler graphical user interface 160 causes another window illustrating the legend to appear, with a "back" button to allow return to the original screen where the bar 300 is shown.

Also, if the user requires further information regarding the individual drugs that were dispensed, then the drug profiler graphical user interface 160 is responsive to clicking on a name icon 350 or touching a portion of the display to provide more detailed information, such as by way of a detailed information screen. The detailed information screen displays details regarding the drug supply matrix 200, such as the dates on which the drug was dispensed over a period of time, such as the past 12 months.

Of course, the drug profiler can be enhanced with many features. For example, the supply matrix 200 may be used to store, in addition to data regarding dispensed drugs, data regarding prescriptions for those drugs. Of interest to this embodiment of the drug profiler is drug prescription data as may be obtained from electronic prescription records 112 received from a local clinical source such as hospital 104 or private clinic 106. As previously described, each electronic prescription record 112 identifies a patient, a prescribing physician, a drug prescribed to the patient, the date of the prescription, a quantity prescribed, a duration of the prescription and a dosage. Thus, the start date for an electronic prescription record 112 is the date on which the drug was prescribed, while dosage and the quantity dispensed are used to compute an artificial end date for that electronic prescription record. Alternatively, the end date may be computable from the duration of the prescription specified in the electronic prescription record itself.

Figure 2B:
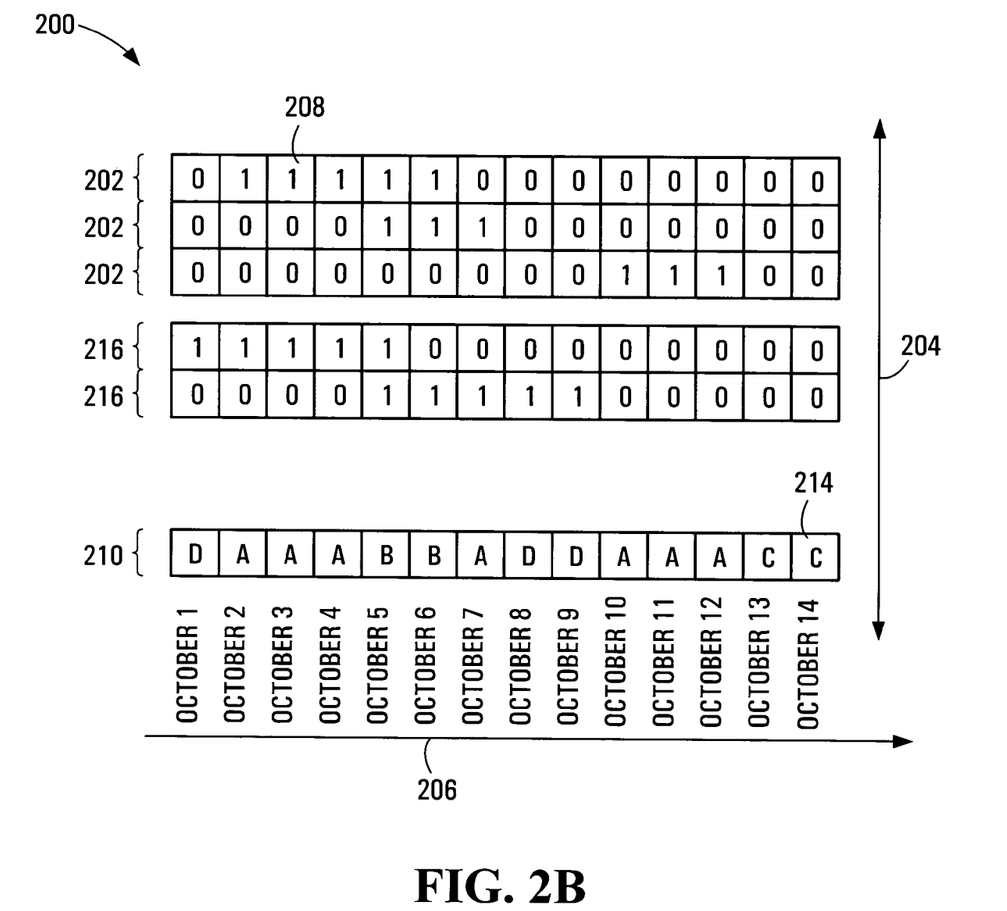

With reference to FIG. 2B, the drug profiler functional entity 150 groups all the electronic prescription records 112 pertaining to the drug in question together as rows 216 of the drug supply matrix 200. The rows 216 corresponding to electronic prescription records 112 appear alongside rows 202 corresponding to dispensed prescription records 110. Each row 216 has a matrix entry 208 for each calendar day along the x-axis 206. For each row 216, the matrix entry 208 corresponding to a particular calendar day between the start date and the end date for the corresponding electronic prescription record 112 will contain a code. In an embodiment, this code may be the same as was used to fill the matrix entries 208 of the rows 202, namely 1=supply available and 0=no supply available.

In this embodiment, the drug profiler functional entity 150 computes the drug supply timeline 210 in much the same manner has already been described. However, to account for the electronic prescription records 112, the following modification is made. If for a given calendar day, the matrix entry 208 in a particular one of the rows 216 contains a "1" and the corresponding entry 214 in the drug supply timeline 210 already contains a "C" (as a result of having processed the rows 202), then this means that the given calendar day is one on which the drug was prescribed but not dispensed. The contents of that entry 214 in the drug supply timeline 210 is accordingly changed from "C" to a different code (e.g., "D") in order to account for this situation. Thus, the drug supply timeline can be made to account for calendar days between the date on which the drug was prescribed and the date on which the drug was actually dispensed.

The drug profiler graphical user interface 160 then supplies the data contained in the drug supply timeline 210 to the display 170, for presentation in a user-friendly manner. Codes "A", "B" and "C", corresponding to time periods where the drug in question is available to different degrees, are displayed as before. Moreover, to account for code "D", corresponding to a time period where the drug is prescribed but not dispensed, is also rendered visually distinguishable on the bar 300. For example, with reference again to FIG. 3, days on which the drug in question was prescribed but not dispensed may be indicated by a continuous portion 308 of the bar 300 that is assigned a distinct color (e.g., the same color as the portion 302 but in a lighter shade, or a different color altogether). This allows a user to assess how long it took for a prescription to be filled, again pointing to potential problems in patient compliance.

Figure 4:
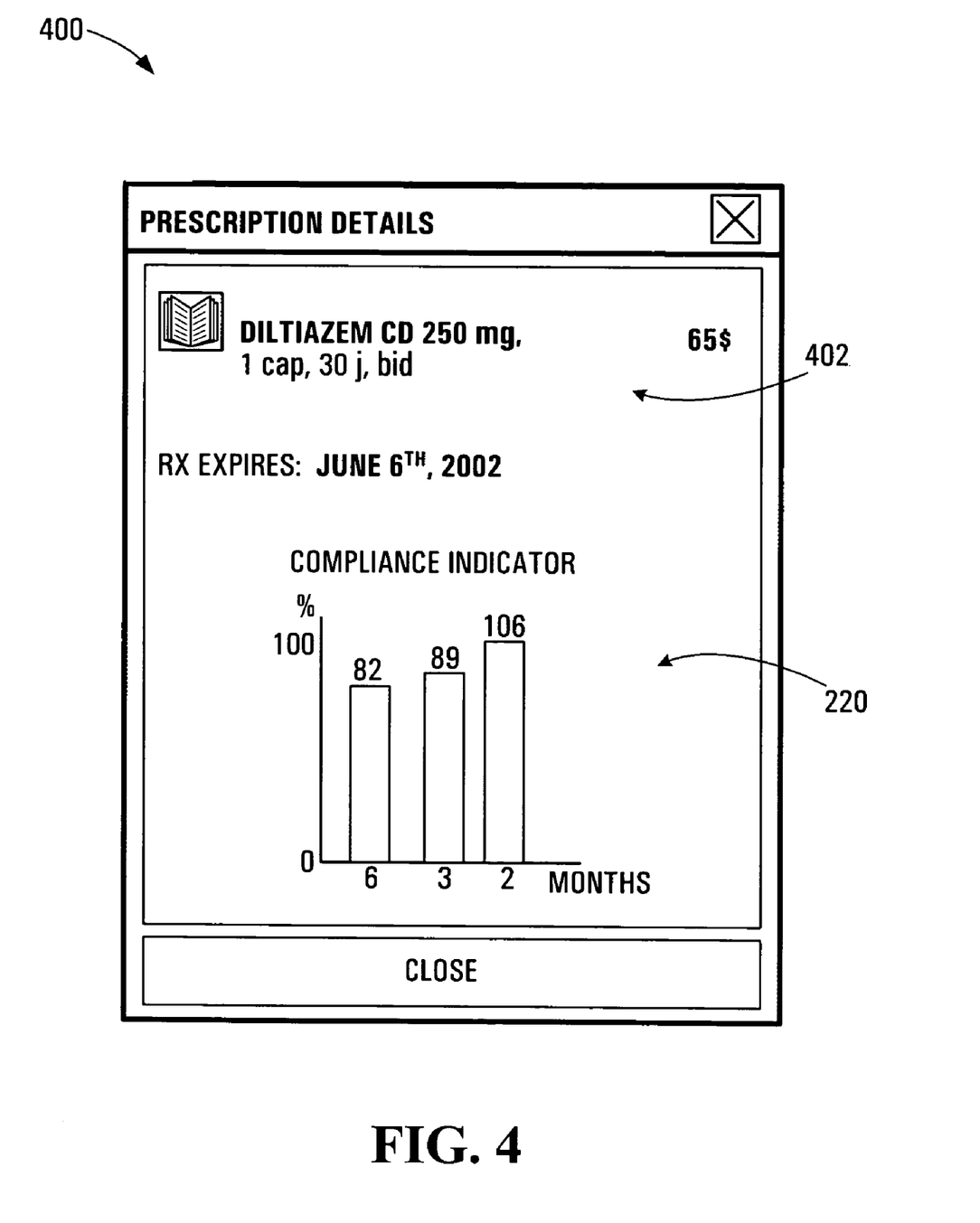
FIG. 4 shows a detailed information screen that is accessible by interfacing with the elements of the screen shot of FIG. 3.

Also, in response to the user accessing the detailed information screen 400 by, say, clicking on or touching the name icon 350, the drug profiler graphical user interface 160 causes the display of further details regarding the drug supply matrix 200, such as prescription data 402 (e.g., the dosage, the various possible names for the drug, the date on which the prescription expires).

Another enhancement of the drug profiler takes into consideration the fact that typically, physicians may provide patients with samples of medication. In this embodiment, the drug supply matrix 200 is further used to store data regarding dispensed samples of the drug in question. Of interest to this embodiment of the drug profiler are the drug sample records 114 as may be received from a local clinical source such as hospital 104 or private clinic 106. As previously described, each drug sample record 114 identifies a patient, the sample drug, the identity of the physician dispensing the sample, the date on which the sample was dispensed, the quantity dispensed, the duration of the sample and the dosage. An expected duration of the sample may also be output or it may readily be computed from the quantity dispensed and the dosage. Thus, the start date for a drug sample record 114 is the date on which the drug sample was dispensed, while dosage and the quantity dispensed are used to compute an end date for that drug sample record. Alternatively, the end date may be computable from the duration of the sample specified in the drug sample record itself.

Figure 2C:
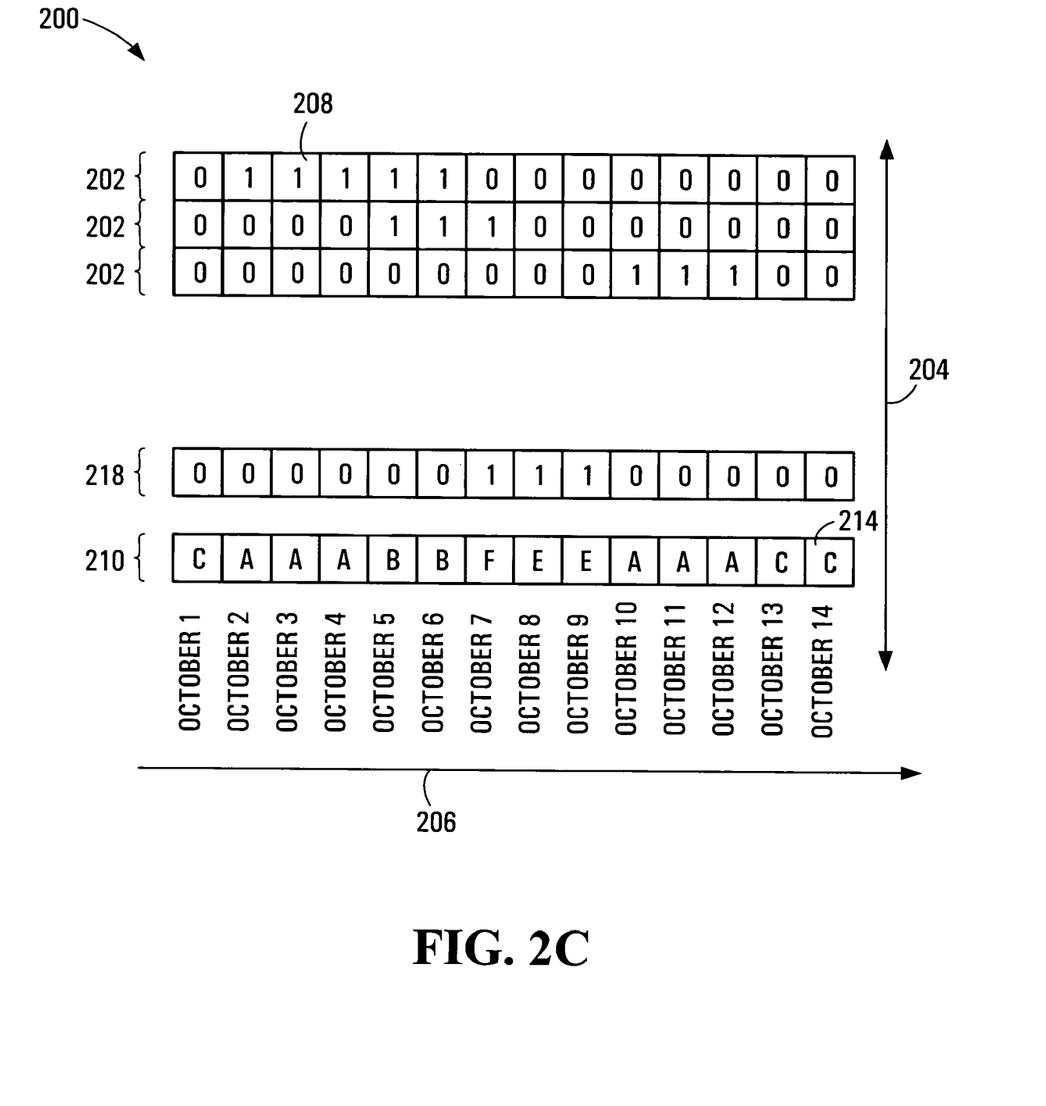

With reference to FIG. 2C, the drug profiler functional entity 150 groups all the drug sample records 114 pertaining to the drug in question together as rows 218 of the drug supply matrix 200. The rows 218 corresponding to drug sample records 114 appear alongside rows 202 corresponding to dispensed prescription records 110 and, optionally, alongside rows 216 corresponding to electronic prescription records 112. Each row 218 has a matrix entry 208 for each calendar day along the x-axis 206. For each row 218, the matrix entry 208 corresponding to a particular calendar day between the start date and the end date for the corresponding drug sample record 114 will contain a code. In an embodiment, this code may be the same as was used to fill the matrix entries 208 of the rows 202 or rows 216, namely 1=supply available and 0=no supply available.

In this embodiment, the drug profiler functional entity 150 computes the drug supply timeline 210 in much the same manner has already been described. However, to account for the drug sample records 114, the following modification is made. If for a given calendar day, the matrix entry 208 in a particular one of the rows 218 contains a "1" and the corresponding entry 214 in the drug supply timeline 210 already contains a "C" (as a result of having processed the rows 202 and, optionally, rows 216), then this means that the given calendar day is one on which the dispensed sample was available in non-duplicate supply. The contents of that entry 214 in the drug supply timeline 210 is accordingly changed from "C" to a different code (e.g., "E") in order to account for this situation. Furthermore, if for a given calendar day, the matrix entry 208 in a particular row 218 contains a "1" and the corresponding entry 214 in the drug supply timeline 210 already contains an "A" or a "B" (as a result of having processed the rows 202), then this means that the given calendar day is one on which the dispensed sample was available in oversupply. The contents of that entry 214 in the drug supply timeline 210 is accordingly changed from "A" or "B" to a different code (e.g., "F") in order to account for this situation.

The drug profiler graphical user interface 160 then supplies the data contained in the drug supply timeline 210 to the display 170, for presentation in a user-friendly manner. Codes "A", "B", "C" and "D" are displayed as before. Moreover, to account for code "E", corresponding to a time period where the sample is dispensed and in non-duplicate supply, this may be indicated by a portion 310 of the bar 300 having a new color. Also, to account for code "F", corresponding to a time period where the sample is dispensed and in oversupply, this may be indicated by a portion (not shown) of the bar 300 having a darker shade of the new color or a separate color altogether. This allows a user to assess the pattern of drug use following the distribution of a sample.

Also, in response to the user accessing the detailed information screen 400 by, say, clicking on or touching the name icon 350, the drug profiler graphical user interface 160 causes the display of further details regarding the drug supply matrix 200, such as the dates on which the drug was dispensed as a sample, over a period of time such as the past 12 months.

It should be appreciated that if samples are to be delivered through the pharmacy network (rather than through doctors' offices), then this does not change the ability of the drug profiler graphical user interface 160 to visually distinguish the sample medication from other drugs. Under such circumstances, the difference would be related to the source of the drug sample record 114, which would change from being a local clinical source (e.g., hospital 104 or private clinic 106) to a remote clinical source (e.g., pharmacy 102).

In accordance with another enhancement of the drug profiler, the drug profiler is adapted to assist a user in assessing refill compliance. Specifically, refill compliance can be defined as the ratio of the amount of medication dispensed to the amount of medication prescribed, during a given time period, e.g., on a monthly basis. In a specific embodiment, the drug profiler functional entity 150 obtains a measure of the amount of medication dispensed by counting the number of "1"'s appearing in the matrix entries 208 of the rows 202 corresponding to the dispensed prescription records 110. Also, the drug profiler functional entity 150 obtains a measure of the amount of medication prescribed by counting the number of "1"'s appearing in the matrix entries 208 of the rows 216 corresponding to the electronic prescription records 112.

The comparison yields a refill compliance indicator 220 that is indicative of the consistency with which the patient is being dispensed the drugs that he or she has been prescribed. There may also be more than one refill compliance indicator 220, one for each of a plurality of time windows (e.g., 2, 3 and 6 months as shown in FIG. 4). The refill compliance feature is particularly useful when all prescriptions are electronic and thus associated with a respective electronic prescription record 112, or where only those dispensed prescription records 110 corresponding to drugs dispensed on the basis of electronic prescriptions are considered.

To avoid under-counting days of drug supply based on past dispensed prescriptions, the drug profiler functional entity 150 may be adapted so as to produce a refill compliance indicator 220 only if there is a significant (e.g., 2-month) past history of dispensed medication. This would account for a reasonable delay between the generation of an electronic prescription record 112 and the actual dispensing of the drug to a patient. In such an example, the refill compliance indicator 220 is not calculated unless data regarding prescriptions dispensed in, say, the past 60 days is available. This approach avoids false-positive identification of compliance problems that would be the result of omitting, as part of the refill compliance assessment, data on drug supply days created by recent and as yet undispensed prescriptions.

The drug profiler graphical user interface 160 then displays the refill compliance indicator 220 on the display 170. In one embodiment, the refill compliance indicator 220 is displayed on the same screen as the drug supply timeline 210 for the drug in question. Alternatively, the refill compliance indicator 220 may be part of the information displayed upon the user acceding to the detailed information screen 400 by clicking on or touching the name icon 350 of the drug in question. The latter scenario is shown in FIG. 4.

Thus, from the above, it will be appreciated that the drug supply matrix 200 can be designed to provide useful information to a user under various circumstances, namely when the drug is prescribed electronically and then dispensed, when the drug is prescribed with no record of dispensation, when the drug is dispensed with no record of an electronic prescription (as a physician may not prescribe electronically), and when samples of the drug are provided through in-office supplies.

In the embodiments heretofore considered, the description has focused on the various dispensed prescription records 110, electronic prescription records 112, drug sample records 114 and prescription claim records 120 being associated with the same drug. In one scenario, the fact that these data records are associated with the same drug is evident from a drug name identified in the received record. However, there are cases where more than one drug name is indicative of the same chemical compound. For example, drug switches may be made because of generic substitution, or supply availability. Thus, it would be advantageous if the drug profiler were equipped with intelligence to recognize this scenario.

To this end, the drug profiler functional entity 150 is adapted to consider pharmacological equivalencies when grouping the rows 202 of the drug supply matrix 200. This is rendered possible by providing the patient care management system 100 with a link to a database 180 of pharmacological equivalencies (see FIG. 1), which can be implemented as a plurality of groups of drug names. Each group is associated with a common chemical name, and is accessible by querying the name of any drug in the group. Thus, for example, upon extracting a particular drug name from a dispensed prescription record 110, this drug name is input to the database 180 to obtain the chemical name of the drug. Thus, when constructing the drug supply timeline 210 for a drug in question, this is extended to cover all drugs sharing a common chemical name. The drug profiler graphical user interface 160 causes the common chemical name of the drug to appear on the display 170 in proximity to the corresponding bar 300.

As previously described, in order to allow the user to access a separate detailed information screen 400 for the drug in question, a name icon 350 is provided in proximity to the bar 300. This name icon 350 may be the chemical name or trademark for the drug in question. By clicking on or touching the name icon 350, the detailed information screen 400 reveals more detailed information regarding the names of the drugs actually prescribed and dispensed. For example, say that a physician prescribes a brand-name medication such as Ativan, and a generic substitution is made at the time of dispensing for apo-lorazepam. The name icon 350 might show "Ativan", but when the detailed information screen 400 is displayed, the prescription for Ativan will be distinguishable from the dispensing of apo-lorazepam. In this way, the user can readily reconcile changes made in the drug prescribed relative to the drug dispensed at the pharmacy, such changes possibly being due to supply constraints or the decision to substitute a generic for a brand name medication.

Other information that may be displayed on the detailed information screen 400 includes a monograph of the selected drug. The monograph may be obtained by the drug profiler functional entity 150 accessing a remote location (e.g., server) via a private data network (such as a hospital LAN) or a public data network (such as the Internet or World Wide Web).

The drug profiler is also adapted to function in the case where multiple distinct drugs (having differing chemical names) have been prescribed/dispensed to the patient. In this scenario, the drug profiler functional entity constructs a drug supply matrix 200 for each such drug, resulting in multiple drug supply timelines 210. The drug profiler graphical user interface 160 then converts the various drug supply timelines 210 into bars 300 that are displayed relative to a common time base, which effectively results in a composite bar graph showing all active medication, as shown in the screen shot of FIG. 3. This composite bar graph includes a display of information regarding each drug, such as its chemical name, by way of name icons 350. The user then accesses a detailed information screen for each active drug by clicking on or touching the appropriate name icon 350, for example.

In a further variant, the drug profiler graphical user interface 160 provides a mechanism for allowing the user to toggle the chemical name that is displayed as the name icon 350. This is useful to accommodate both those physicians that may feel more familiar with a generic drug name and others that may be more familiar with the brand name drug. To this end, a mechanism such as a screen button 360 can be provided to allow the user to select whether the generic name or trade mark is to be displayed. The screen button 360 can be provided for each of the active drugs or for all active drugs simultaneously, as is the case with the screen button 360 in FIG. 3. This function enables a user to view the list of current drugs in accordance with the naming convention with which he or she is most familiar.

In another variant, the drug profiler is also adapted to function in the case where multiple distinct physicians have been prescribing drugs for the patient. In accordance with this variant, the drug profiler functional entity 150 enhances the drug supply matrix 200 so as to store data regarding the prescribing physician for each drug. Of interest to this embodiment of the drug profiler is drug prescription data as may be obtained from electronic prescription records 112 received from a local clinical source such as hospital 104 or private clinic 106, as well as from dispensed prescription records 110 received from a remote clinical source such as pharmacy 102. As previously described, the electronic prescription records 112 and the dispensed prescription records 110 identify a prescribing physician (e.g., by license number). The drug profiler functional entity 150 matches this data with the identification number of the prescribing physician (e.g., by license number, personal identification number, machine identification number) who has been authorized by the patient to access their drug profile.

The functional entity then encodes the data regarding the prescribing physician within the entries 208 of the drug supply matrix 200. The drug profiler graphical user interface 160 then merges the drug supply timeline 210 with the prescribing physician data. In order to render the display less confusing and increase confidentiality, the drug profiler graphical user interface 160 can present portions of each bar 300 in a first color when the prescription for the drug is issued by the prescribing physician (who is assumed to be the user of the patient care management system), while a second color is used to present all other prescriptions. If the same patient's profile is viewed by another physician, the graphical user interface applies the color-coding scheme relative to the other physician. Thus, a color-coded scheme of this nature can accommodate the usual situation where a patient may be seen and have drugs prescribed by multiple physicians. Also, it should be understood that color is but one of myriad ways in which a distinction between or amongst physicians can be presented by the drug profiler graphical user interface 160.

In a further variant of the patient care management system 100, the drug profiler functional entity 150 performs a drug review and alert procedure. The drug review and alert procedure can be set up to occur on demand only, or automated prior to the submission of a prescription by the prescribing physician. The drug profiler graphical user interface 160 may also provide a mechanism for allowing the user to set the sensitivity of the drug review and alert procedure at multiple settings of severity of prescribing problem.

The drug review and alert procedure involves the drug profiler functional entity processing the health problem list 116 (which is indicates the medical conditions that the patient is suffering from) in conjunction with the aversion list 118, in order to signal an alert with respect to problematic medication. To this end, the drug profiler functional entity 150 has access to a drug knowledge database 190 containing drug-drug interaction data and drug-disease interaction data.

Under the drug review and alert procedure, the drug profiler functional entity 150 submits the identity of the drugs that have been prescribed or dispensed to the patient, along with the dosage (optionally), to the drug knowledge database 190 to perform a drug-drug contraindications verification in order to isolate whether any of the drugs dispensed to the patient are likely to adversely interact with one another. In addition, the drug profiler functional entity 150 submits the identity of the dispensed drugs along with dosage (optional), the health problem list 116 and the aversion list 118 to the drug knowledge database 190 to perform a drug-disease verification in order to isolate whether any of the drugs dispensed to the patient are likely to cause adverse side effects given the patient's particular medical condition. This verification may also take into account other factors, such as the age of the patient, as provided in the prescription claim records 120 received from an administrative information source such as insurance company 108. By way of non-limiting example, five possible categories of contraindications that can be verified as part of the drug review and alert procedure include:

1) drug-age contraindications (e.g. long-acting benzodiazepines for persons 65 years of age or older);

2) drug-disease contraindications (e.g peptic ulcer disease and NSAIDs);
3) drug-drug interactions (e.g. anticoagulant and a sulfonamide);
4) therapeutic duplication (e.g. two H2 antagonists (cimetidine & rantidine);
5) excess dose (triazolam>0.25 mg).

If, during the drug review and alert procedure, the drug profiler functional entity 150 detects a problem, then the drug profiler graphical user interface 160 displays a warning icon 370 beside the drug(s) that triggered the alert. To identify the nature of the problem, the user clicks on or touches the warning icon 370, causing the drug profiler graphical user interface 160 to open the detailed information screen 400, where details of the potential prescribing problem are displayed. Alternatively, the screen displayed by the graphical user interface 160 may be a new detailed information screen different from the detailed information screen 400 previously described. Myriad other ways of conveying the requisite alert information are within scope of the present invention and will be readily implemented by a person of ordinary skill in the art.

If running the drug review and alert procedure results in the issuance of a warning, then the drug profiler functional entity 150 may be programmed to prevent the issuance of further electronic prescriptions for the patient by communicating with other entities (not shown) within the patient care management system. In some implementations, the user may be empowered to override an alert for a particular drug. Under this embodiment, the drug profiler graphical user interface 160 presents a menu of possible reasons for the over-ride decision, and the user clicks a check-box to identify the reason. Alert over-rides and reasons for ignoring an alert may be logged by the drug profiler functional entity 150 as part of an audit for each physician/user. Myriad other ways of conveying the requisite over-ride information are within scope of the present invention and will be readily implemented by a person of ordinary skill in the art.

In yet a further variant, the drug profiler functional entity 150 determines the monthly cost of dispensed prescriptions. This can be done by extracting cost data from the dispensed prescription records 110 as well as the prescription claim records 120. The drug profiler functional entity 150 determines the total cost of prescriptions (e.g., drug+dispensing fee) dispensed in a given time period by summing the costs for each prescription dispensed in the time period. The drug profiler graphical user interface 160 then displays this information as, say, the dollar amount for each month.

In yet another variant, the drug profiler functional entity 150 processes the dispensed prescription records 110 and/or the prescription claim records 120 to determine the mean cost of the dispensed prescriptions on a per-drug basis. The drug profiler graphical user interface 160 presents this data to the user in any convenient way.

Furthermore, it is noted that prescription claim records 120 typically indicate the contribution to the total drug cost paid by the insured patient. Thus, in a variant, the drug profiler functional entity 150 is adapted to sum the drug-specific amounts for a given time period (e.g., month). The drug profiler graphical user interface 160 then displays this data as the total monthly cost that patients paid for their drugs in the given time period. This data may be relevant to a physician or to individuals performing demographic studies because of the insight it provides into the relationship between the amount paid by a patient and the tendency of the patient to purchase the medication (which can be gleaned from the refill compliance indicator 220).

In another enhancement to the drug profiler, the drug profiler functional entity is adapted to gather data indicative of emergency room visits or hospitalization periods. This data is available from the medical service claim records 122. Specifically, the location of service specified by a medical service claim record 122 indicates whether the service was delivered in an emergency room (ER), out-patient clinic, in-patient hospital setting, private clinic, etc. The location code for, say, ER, is combined with the dates of visits billed for from the ER setting, to produce a patient location timeline (not shown) similar to the drug supply timeline 210. A similar approach is used to identify, within the patient location timeline, periods of time when the patient was hospitalized. The drug profiler graphical user interface 160 can depict the patient location timeline in a color-coded fashion (e.g., as a set of bars 380) to show when the patient was treated in the ER, when he or she was hospitalized, etc.

Since primary care physicians are generally not notified if their patient visits the ER, this feature provides a user with information about the occurrence and dates of ER visits, alerting such user to potential treatment problems. It may also be used for advanced decision support modules (e.g., management of asthma). Moreover, the user is also provided with information about the occurrence and dates of hospitalization, which is useful for at least three reasons: 1) physicians may not be aware that their patient has been hospitalized, 2) drugs dispensed during hospital stays are not recorded in prescription claims data and thus gaps in drug supply during periods of hospitalization can be readily visualized, and 3) drugs are often changed during hospitalization, and prior medication prescribed by the physician may not have been stopped/modified to fit with the patient's new treatment regimen.

Those skilled in the art will appreciate that in some embodiments, the functionality of the drug profiler may be implemented as pre-programmed hardware or firmware elements (e.g., application specific integrated circuits (ASICs), electrically erasable programmable read-only memories (EEPROMs), etc.), or other related components. In other embodiments, the drug profiler may be implemented as an arithmetic and logic unit (ALU) having access to a code memory (not shown) which stores program instructions for the operation of the ALU. The program instructions could be stored on a medium which is fixed, tangible and readable directly by the drug profiler, (e.g., removable diskette, CD-ROM, ROM, or fixed disk), or the program instructions could be stored remotely but transmittable to the drug profiler via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

While specific embodiments of the present invention have been described and illustrated, it will be apparent to those skilled in the art that numerous modifications and variations can be made without departing from the scope of the invention as defined in the appended claims.

What is claimed is:

1. A patient care management system for assisting physicians in their treatment of patients, comprising:
   a computer server having access to program instructions for allowing the computer server to implement:
   an input device, said input device being adapted to receive drug dispensation data for at least one drug from different drug prescribing or dispensation entities;

a control device adapted to, for each drug of the at least one drug:
  a) encode said drug dispensation data received from the different drug prescribing or dispensation entities in a drug supply matrix; said drug supply matrix comprising multiple entries of the same drug for each calendar day within a calendar period extending at least between a start date and an end date, each entry being received from a different drug prescribing or dispensation entity and being indicative of one of an availability and an unavailability of the drug on a given calendar day; and
  b) for each calendar day of the calendar period, consolidate said multiple entries of the drug supply matrix into a single entry, each single entry being indicative of a degree of supply availability for the drug, said degree of supply availability being one of a non-duplicated supply, an oversupply, and an insufficient supply of the drug on the given calendar day; and
  c) encode each of said single entries into a drug supply timeline matrix for each calendar day within the calendar period; and
an output adapted to release the drug supply timeline matrix for each drug of the at least one drug for display to a physician, wherein drug supply timeline matrices for more than one drug are combinedly displayed in a drug profiler matrix including multiple lines, each line corresponding to a particular drug and including a visual indication of the degree of supply availability for the particular drug.

2. The system defined in claim 1, wherein the drug dispensation data for the one drug includes a dispensation record indicative of an identity of the one drug, a date of dispensation, a dispensed quantity and a dosage.

3. The system defined in claim 2, wherein the control device is further adapted to process the dispensation record to identify at least one calendar day during which the one drug identified in said dispensation record is expected to have been available, wherein the at least one calendar day is one of the start date and the end date, the start date corresponding with the date of dispensation identified in said dispensation record, and the end date corresponding with an expected end date for said dispensation record.

4. The system defined in claim 3, wherein the drug dosage identified in said dispensation record is a daily dosage and wherein the control device is further adapted to determine the end date by counting, from the date of dispensation identified in said dispensation record, a number of days equal to the quotient of the dispensed quantity identified in said dispensation record and the drug dosage identified in said dispensation record.

5. The system defined in claim 3, wherein the drug dosage identified in said dispensation record is a non-daily dosage, wherein the control device is further adapted to compute a daily dosage from the non-daily dosage and to determine the end date by counting, from the date of dispensation identified in said dispensation record, a number of days equal to the quotient of the dispensed quantity identified in said dispensation record and the daily dosage.

6. The system defined in claim 1, wherein the control device is further adapted to identify a period of time associated with a same degree of availability for the one drug, the period of time corresponding to one or more consecutive calendar days falling between the start date and the end date of one dispensation record identifying the one drug.

7. The system defined in claim 1, wherein: the input device is further adapted to receive prescription data regarding a particular drug corresponding to one of the at least one dispensed drug, the prescription data including a prescription record indicative of an identity of the particular drug, a date of prescription, a prescribed quantity and a prescribed dosage; the control device is further adapted to: (i) determine, from the dispensation record identifying the particular drug, an amount of the particular drug dispensed in a predetermined time period; (ii) determine, from the prescription data identifying the particular drug, an amount of the particular drug prescribed in the predetermined time period; (iii) determine an indication of refill compliance for the predetermined time period from the amount of the particular drug dispensed and the amount of the particular drug prescribed; and the output device is further adapted to release the indication of refill compliance.

8. The system defined in claim 7, wherein the control device being adapted to determine the indication of refill compliance comprises the control device being adapted to determine a ratio between a total number of time units during which the particular drug is expected to have been available to the patient and a total number of time units during which the particular drug was prescribed but not dispensed to the patient, the indication of refill compliance being a function of said ratio.

9. The patient care management system defined in claim 1, wherein the input device is configured to receive data regarding a plurality of drugs dispensed to the patient, and wherein the control device is further adapted to perform a drug-drug contraindications verification of the drugs dispensed to the patient; the output device further being adapted to release data indicative of the drug-drug contraindications verification.

10. The system defined in claim 9, wherein the control device being adapted to perform a drug-drug contraindications verification of the drugs dispensed to the patient comprises the control device being adapted to access a database to attempt to identify one or more contraindicated drugs.

11. The system defined in claim 10, wherein the data indicative of the drug-drug contraindications verification comprises data which, when displayed, allows a user to distinguish a contraindicated drug from among the plurality of drugs dispensed to the patient.

12. The system defined in claim 9, the input device being further adapted to obtain data regarding at least one ailment with which the patient is afflicted, the control device being further adapted to perform a drug-ailment contraindications verification of the drugs dispensed to the patient, the output device being further adapted to release data indicative of the drug-ailment contraindications verification.

13. The system defined in claim 12, wherein the control device being adapted to perform a drug-ailment contraindications verification of the drugs dispensed to the patient comprises the control device being adapted to access a database to attempt to identify one or more contraindicated drugs.

14. The system defined in claim 13, wherein the data indicative of the drug-ailment contraindications verification comprises data which, when displayed, allows a user to distinguish a contraindicated drug from among the plurality of drugs dispensed to the patient.

15. The system defined in claim 9, the input device being further adapted to obtain data regarding at least one drug aversion associated with the patient, the control device being further adapted to perform a drug-aversion verification of the drugs dispensed to the patient, the output device being further adapted to release data indicative of the drug-aversion verification.

16. The system defined in claim 15, wherein the control device being adapted to perform a drug-aversion verification of the drugs dispensed to the patient comprises the control device being adapted to cross-reference the data regarding at least one drug aversion with the data regarding the plurality of drugs dispensed to the patient to attempt to identify one or more contraindicated drugs.

17. The system defined in claim 16, wherein the data indicative of the drug-aversion verification comprises data which, when displayed, allows a user to distinguish a contraindicated drug from among the plurality of drugs dispensed to the patient.

18. The system defined in claim 17, the input device being further adapted to obtain data regarding an age of the patient, the control device being further adapted to perform a drug-age verification of the drugs dispensed to the patient, the output device being further adapted to release data indicative of the drug-age verification.

19. The system defined in claim 18, wherein the control device being adapted to perform a drug-age verification of the drugs dispensed to the patient comprises the control device being adapted to access a database to attempt to determine one or more contraindicated drugs.

20. The system defined in claim 19, wherein the data indicative of the drug-age verification comprises data which, when displayed, allows a user to distinguish a contraindicated drug from among the plurality of drugs dispensed to the patient.

21. The patient care management system defined in claim 1, wherein the input device is further adapted to receive data regarding at least one insurance claim for medical services; and
wherein the control device is further adapted to determine from the data regarding the at least one insurance claim for medical services a feature of the medical services claimed in the at least one insurance claim;
the output device further being adapted to release data indicative of the feature of the medical services claimed in the at least one insurance claim.

22. The system defined in claim 21, wherein the input device being adapted to receive data regarding the at least one insurance claim comprises the input device being adapted to receive at least one of the at least one insurance claim from a government insurer.

23. The system defined in claim 21, wherein the input device being adapted to receive data regarding the at least one insurance claim comprises the input device being adapted to receive at least one of the at least one insurance claim from a private insurer.

24. The system defined in claim 21, wherein the data regarding a particular one of the at least one insurance claim includes a date when at least one prescription drug identified was dispensed, a cost of the at least one prescription drug and an insured individual's contribution towards the cost of the at least one prescription drug.

25. The system defined in claim 24, wherein the control device being adapted to determine a feature of the medical services claimed in the at least one insurance claim comprises the control device being adapted to determine a monthly cost of the at least one prescription drug.

26. The system defined in claim 25, wherein the control device being adapted to determine a feature of the medical services claimed in the at least one insurance claim comprises the control device being adapted to determine the insured individual's contribution to the monthly cost of the at least one prescription drug.

27. The system defined in claim 24, wherein the at least one prescription drug includes a plurality of prescription drugs, wherein the control device being adapted to determine a feature of the medical services claimed in the at least one insurance claim comprises the control device being adapted to determine a mean cost of the plurality of prescription drugs.

28. The system defined in claim 21, wherein the data regarding each particular one of the at least one insurance claim includes data indicative of a date when and a location where the services claimed in the particular insurance claim were performed.

29. The system defined in claim 28, wherein the control device being adapted to determine a feature of the medical services claimed in the at least one insurance claim comprises the control device being adapted to determine a period of time during which the services claimed in the at least one insurance claim were performed at a common location.

30. The system defined in claim 29, wherein the data indicative of the feature of the medical services claimed in the at least one insurance claim comprises data which, when displayed, allows a user to distinguish said period of time with respect to a time window.

31. The system defined in claim 30, wherein the time window is user-selectable.

32. The system defined in claim 28, wherein the common location is selected from the group consisting of an emergency room, an in-patient hospital setting, an out-patient clinic and a private clinic.

33. A patient care management system, comprising:
a computer server having access to program instructions for allowing the server to implement:
an input device adapted to receive, from different drug prescribing or dispensation entities, data regarding a plurality of drugs which are at least one of drugs dispensed to a patient and drugs prescribed to the patient;
a control device adapted to:
(i) determine groups of pharmacologically equivalent drugs from the plurality of drugs;
(ii) for each group of pharmacologically equivalent drugs, encode the data regarding the drugs in a particular group in a drug supply matrix, said drug supply matrix including multiple entries of at least one drug from the particular group for a given calendar day, each entry being received from a different drug prescribing or dispensation entity and being indicative of one of an availability and an unavailability of the drug on the given calendar day;
(iii) for each calendar day within a calendar period, consolidate said multiple entries of the drug supply matrix into a single entry, each single entry being indicative of a degree of drug supply availability for the particular group of pharmacologically equivalent drugs, the drug supply availability data being one of a non-duplicated supply, an oversupply, and an insufficient supply of the drugs in the particular group, per each given calendar day within a calendar period; and
(iv) encode each of said single entries into a drug supply timeline matrix for each calendar day within the calendar period ; and
an output device adapted to release the drug supply timeline matrix for each group of pharmacologically equivalent drugs for display to a physician, wherein drug supply timeline matrices for more than one drug are combinedly displayed in a drug profiler matrix including multiple lines, each line corresponding to a particular drug and including a visual indication of the degree of supply availability for the particular drug.

34. The system defined in claim 33, wherein the data regarding at least one of the plurality of drugs comprises at least one of drug dispensation data and drug prescription data, respectively, and wherein the control device being adapted to combinedly process the data regarding the drugs in a particular one of said groups of pharmacologically equivalent drugs comprises the control device being adapted to determine the drug supply availability data for the particular group of pharmacologically equivalent drugs from the at least one of drug dispensation data and drug prescription data regarding the drugs in the group of pharmacologically equivalent drugs.

35. The system defined in claim 34, wherein the control device being adapted to combinedly process the data regarding the drugs in a particular one of said groups of pharmacologically equivalent drugs comprises the control device being adapted to determine an indication of refill compliance for the particular group of pharmacologically equivalent drugs from the at least one of drug dispensation and drug prescription data regarding the drugs in the particular group of pharmacologically equivalent drugs.

36. A method of implementing a graphical user interface suitable for use in patient care management, comprising:
   receiving from a first drug prescribing or dispensation entity in a computer server, data regarding a first period of time representative of a drug being available to a patient;
   receiving from a second drug prescribing or dispensation entity in the computer server, data regarding a second period of time representative of the drug being available to the patient; said first drug prescribing or dispensation entity being different from the second drug prescribing or dispensation entity;
   displaying on a display device, the first period of time and the second period of time with respect to a common time base in a drug supply matrix comprising multiple entries of the same drug for each calendar day within a calendar period extending at least between a start date and an end date, each entry being received from a different drug prescribing or dispensation entity and being indicative of one of an availability and an unavailability of the drug on a given calendar day;
   for each calendar day of the calendar period, consolidating said multiple entries of the drug supply matrix into a single entry, each single entry being indicative of a degree of supply availability for the drug, said degree of supply availability being one of a non-duplicated supply, an oversupply, and an insufficient supply of the drug on the given calendar day;
   encoding each of said single entries into a drug supply timeline matrix for each calendar day within the calendar period; and
   displaying the degree of supply availability encoded in the drug supply timeline matrix on the display device, as a visual indication, wherein drug supply timeline matrices for more than one drug are combinedly displayed in a drug profiler matrix including multiple lines, each line corresponding to a particular drug and including a visual indication of the degree of supply availability for the particular drug.

37. The method defined in claim 36, comprising: receiving in the server, data regarding a first manner of dispensing a first one of at least one prescription drug to a patient over a first period of time;
   receiving in the server, data regarding a second manner of dispensing a second one of the at least one prescription drug to the patient over a second period of time; the displaying comprising displaying the first and the second periods of time with respect to the common time base; and the providing comprising providing another visual indication to allow a user to distinguish between the first and second manners of dispensing.

38. The method defined in claim 37, wherein the first manner of dispensing includes filling a prescription at a pharmacy and wherein the second manner of dispensing includes distributing a sample.

39. The method defined in claim 36, comprising:
   receiving in the server, data regarding at least one drug dispensed to the patient;
   receiving in the server, data regarding at least one drug prescribed but not dispensed to the patient; and
   jointly displaying the data regarding the at least one drug dispensed to the patient and the data regarding the at least one drug prescribed but not dispensed to the patient.

40. The method defined in claim 39, wherein receiving data regarding a particular one of the at least one drug prescribed to the patient comprises receiving an electronic prescription for the particular drug.

41. The method defined in claim 40, wherein jointly displaying the data regarding the at least one drug dispensed to the patient and the data regarding the at least one drug prescribed but not dispensed to the patient comprises displaying one of: a generic name and a trade name for each of said drugs.

42. The method defined in claim 41, further comprising receiving a desired display format that is indicative of one of a brand name display format and a generic name display format, wherein the displaying one of the generic name and the trade name for each of said drugs is conditional upon the desired display format.

43. The method defined in claim 36, comprising:
   receiving in the server, data regarding a plurality of drugs dispensed to the patient, wherein the data regarding each particular drug includes an identity of a prescribing physician for the particular drug;
   receiving in the server, data regarding the identity of a prescribing physician; wherein the displaying comprises displaying data regarding the drugs dispensed to the patient by providing a another visual indication on the display device that allows a user to distinguish between a first set of drugs for which the prescribing physician is the prescribing physician and a second set of drugs for which the prescribing physician is a physician other than the prescribing physician.

* * * * *